United States Patent
Yuan et al.

(10) Patent No.: US 12,175,303 B2
(45) Date of Patent: Dec. 24, 2024

(54) ADAPTIVELY REALLOCATING RESOURCES OF RESOURCE-CONSTRAINED DEVICES

(71) Applicant: Deere & Company, Moline, IL (US)

(72) Inventors: Zhiqiang Yuan, San Jose, CA (US); Rhishikesh Pethe, Dublin, CA (US); Francis Ebong, San Francisco, CA (US)

(73) Assignee: Deere &Company, Moline, IL (US)

( * ) Notice: Subject to any disclaimer, the term of this patent is extended or adjusted under 35 U.S.C. 154(b) by 680 days.

(21) Appl. No.: 17/485,903

(22) Filed: Sep. 27, 2021

(65) Prior Publication Data
US 2023/0102495 A1    Mar. 30, 2023

(51) Int. Cl.
*G06F 9/50* (2006.01)
*G01N 33/24* (2006.01)
(Continued)

(52) U.S. Cl.
CPC ........... *G06F 9/5094* (2013.01); *G01N 33/24* (2013.01); *G06F 9/5016* (2013.01);
(Continued)

(58) Field of Classification Search
None
See application file for complete search history.

(56) References Cited

U.S. PATENT DOCUMENTS 7,464,147 B1 *  12/2008  Fakhouri ................ G06Q 10/04
                                                            709/223
8,131,843 B2 *  3/2012   Yellin ................... G06F 11/3433
                                                            709/224
(Continued)

OTHER PUBLICATIONS

Heinzle et al., "Computational Stereo Camera System with Programmable Control Loop" ACM Transactions on Graphics, vol. 30, Issue 4, Jul. 2011, Article No. 94, pp. 1-10. Retrieved from https://doi.org/10.1145/2010324.1964989.
(Continued)

*Primary Examiner* — Eric C Wai
(74) *Attorney, Agent, or Firm* — Hanley, Flight & Zimmerman, LLC

(57) ABSTRACT

Implementations are disclosed for adaptively reallocating computing resources of resource-constrained devices between tasks performed in situ by those resource-constrained devices. In various implementations, while the resource-constrained device is transported through an agricultural area, computing resource usage of the resource-constrained device ma may be monitored. Additionally, phenotypic output generated by one or more phenotypic tasks performed onboard the resource-constrained device may be monitored. Based on the monitored computing resource usage and the monitored phenotypic output, a state may be generated and processed based on a policy model to generate a probability distribution over a plurality of candidate reallocation actions. Based on the probability distribution, candidate reallocation action(s) may be selected and performed to reallocate at least some computing resources between a first phenotypic task of the one or more phenotypic tasks and a different task while the resource-constrained device is transported through the agricultural area.

20 Claims, 7 Drawing Sheets

(51) Int. Cl.
*G06F 11/30* (2006.01)
*G06F 17/18* (2006.01)

(52) U.S. Cl.
CPC .......... *G06F 11/3058* (2013.01); *G06F 17/18* (2013.01); *G01N 33/245* (2024.05)

(56) References Cited

U.S. PATENT DOCUMENTS

| | | | |
|---|---|---|---|
| 8,666,241 | B2 | 3/2014 | Cameron et al. |
| 8,754,929 | B1 | 6/2014 | Prince |
| 9,237,331 | B2 | 1/2016 | Heinzle et al. |
| 10,694,686 | B2 | 6/2020 | Xu |
| 10,937,193 | B2 | 3/2021 | Hu et al. |
| 2008/0004940 | A1* | 1/2008 | Rolleston Phillips ........................ G06Q 10/06375 705/7.31 |
| 2020/0019777 | A1 | 1/2020 | Gurzoni, Jr. et al. |
| 2020/0120267 | A1 | 4/2020 | Stelmar Netto et al. |
| 2021/0158041 | A1 | 5/2021 | Chowdhary et al. |
| 2022/0092705 | A1 | 3/2022 | Khait |

OTHER PUBLICATIONS

Adams et al., "The Frankencamera: An Experimental Platform for Computational Photography" Communications of the ACM. vol. 55, No. 11. Dated Nov. 2012.
Paul et al., "CamTuner: Reinforcement-Learning based System for Camera Parameter Tuning to enhance Analytics" arXiv:2107.03964v1 [cs.LG] dated Jul. 8, 2021.
Agarwal et al., "Perception System for Autonomous Driving" Carnegie Mellon the Robotics Institute. Dated May 6, 2017. 36 pages.
Todd Vorenkamp, "The Benefits for Using Auto Modes on Your Digital Camera" B&H Explora. Retrieved from www.bhphotovideo.com/explora/photography/tips-and-solutions/benefits-using-auto-modes-your-digital-camera. Dated Sep. 1, 2021. 4 pages.
Sheng et al., "Deep Reinforcement Learning-Based Task Scheduling in IoT Edge Computing." Sensors 2021, 21, 1666. Retrieved from doi.org/10.3390/s21051666.
Zhang et al., "Resource Allocation for a UAV-Enabled Mobile-Edge Computing System: Computation Efficiency Maximization" IEEE Access. Digital Object Identifier. doi.10.1109/ACCESS.2019.2935217. Dated Aug. 28, 2019. 10 pages.
Binas et al., "Reinforcement Learning for Sustainable Agriculture" in Proceedings of the International Conference on Machine Learning Workshop, 2019.
Nassar et al., "Reinforcement Learning-based Resource Allocation in Fog RAN for IoT with Heterogeneous Latency Requirements" arXiv:1806.04582v2 [cs.NI] dated Jan. 15, 2019. 11 pages.
Meng et al., "Power Allocation in Multi-User Cellular Networks: Deep Reinforcement Learning Approaches" arXiv:1901.07159v1 [cs.IT] Dated Jan. 22, 2019. 29 pages.
Yan et al., "Offloading and Resource Allocation with General Task Graph in Mobile Edge Computing: A Deep Reinforcement Learning Approach" arXiv:2002.08119v1 [cs.NI] dated Feb. 19, 2020. 31 pages.
Liakos et al., "Machine Learning in Agriculture: A Review" Sensors. 2018. 18, 2674; doi:10.3390/s18082674. 29 pages.
Baek et al., "Heterogeneous Task Offloading and Resource Allocations via Deep Recurrent Reinforcement Learning in Partial Observable Multi-Fog Networks" arXiv:2007.10581v1 [cs.DC] dated Jul. 21, 2020. 16 pages.
Zhan et al., "Deep Reinforcement Learning-Based Offloading Scheduling for Vehicular Edge Computing" IEEE Internet of Things. Dated May 26, 2020. 28 pages.

\* cited by examiner

ADAPTIVELY REALLOCATING RESOURCES OF RESOURCE-CONSTRAINED DEVICES

BACKGROUND

Various types of devices may be carried across geographic areas such as agricultural fields in order to gather and/or process sensor data and/or to make a variety of different inferences. For example, vision sensor(s) may be integral with a modular computing device that is mounted to a tractor or other agricultural vehicle and transported across a field, or integral with a mobile robot, in order to capture images of crops. These captured images may be processed in situ using techniques such as artificial intelligence and machine learning to generate various inferences, such as visual annotations, fruit/vegetable count estimates, crop yields, disease detection, plant health assessment, etc. However, these modular computing devices and/or robots may suffer from resource constraints such as limited battery power, limited memory, limited processing power, etc. Moreover, these computational tasks may be computationally expensive, and the agricultural areas in which they are performed may be exceedingly large.

SUMMARY

Implementations are described herein for adaptively reallocating computing resources of resource-constrained devices between tasks performed in situ by those resource-constrained devices. Techniques described herein may optimize usage of computing resources by resource-constrained devices, enabling those resource-constrained devices to operate for longer periods of time and/or cover larger areas without needing to be recharged or otherwise serviced. For example, techniques described herein may ensure that a modular computing node or robot is able to be transported through an entire field before it requires a recharge. As used herein, a "resource-constrained device" may include, for instance, a battery-powered modular computing device that may or may not include integral sensors, a robot with one or more sensors, or any other device capable of transporting itself or being transported through an agricultural area while performing tasks.

In some implementations, a method may implemented by a resource-constrained device while the resource-constrained device is transported through an agricultural area. The method may include: monitoring computing resource usage of the resource-constrained device; monitoring phenotypic output generated by one or more phenotypic tasks performed onboard the resource-constrained device; generating a state based on the monitored computing resource usage and the monitored phenotypic output; processing the state based on a policy model to generate a probability distribution over a plurality of candidate reallocation actions; and based on the probability distribution, selecting and performing one or more of the candidate reallocation actions to reallocate at least some computing resources between a first phenotypic task of the one or more phenotypic tasks and a different task while the resource-constrained device is transported through the agricultural area.

In various implementations, the one or more phenotypic tasks comprise a plurality of phenotypic tasks, and the different task comprises a second phenotypic task of the plurality of phenotypic tasks. In various implementations, the different task comprises a new phenotypic task outside of the one or more phenotypic tasks.

In various implementations, the state is further generated based on an amount of battery power required for the resource-constrained device to achieve one or more goals. In various implementations, the one or more goals include performance of the one or more phenotypic tasks over at least a threshold amount of the agricultural area.

In various implementations, the state is further generated based on one or more environmental conditions of the agricultural area. In various implementations, the monitored phenotypic output signals potential presence of a phenotypic condition, and the different task includes application of a machine learning model trained to detect presence of the phenotypic condition. In various implementations, the phenotypic condition comprises plant disease infection or pest infestation. In various implementations, the phenotypic condition comprises plant dehydration or over-hydration.

In various implementations, the method may further include causing an output device to render output conveying an effect the selected one or more candidate reallocation actions will have on the first phenotypic task. In various implementations, the output may include a prompt seeking approval to perform the selected one or more candidate reallocation actions.

In various implementations, the selected one or more candidate reallocation actions include decreasing processor cycles assigned to the first phenotypic task and increasing processor cycles assigned to the different task. In various implementations, the selected one or more candidate reallocation actions include decreasing memory allocated to the first phenotypic task and increasing memory allocated to the different task.

In various implementations, the selected one or more candidate reallocation actions include decreasing network bandwidth allocated to the first phenotypic task and increasing network bandwidth allocated to the different task. In various implementations, the selected one or more candidate reallocation actions include decreasing inter-core bandwidth allocated to the first phenotypic task and increasing inter-core bandwidth allocated to the different task.

In addition, some implementations include one or more processors (e.g., central processing unit(s) (CPU(s)), graphics processing unit(s) (GPU(s)), and/or tensor processing unit(s) (TPU(s)) of one or more computing devices, where the one or more processors are operable to execute instructions stored in associated memory, and where the instructions are configured to cause performance of any of the aforementioned methods. Some implementations also include one or more non-transitory computer readable storage media storing computer instructions executable by one or more processors to perform any of the aforementioned methods. Yet other implementations include agricultural vehicles, such as robots, that are equipped with edge processor(s) configured to carry out selected aspects of the present disclosure.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein.

DETAILED DESCRIPTION

Figure 1:
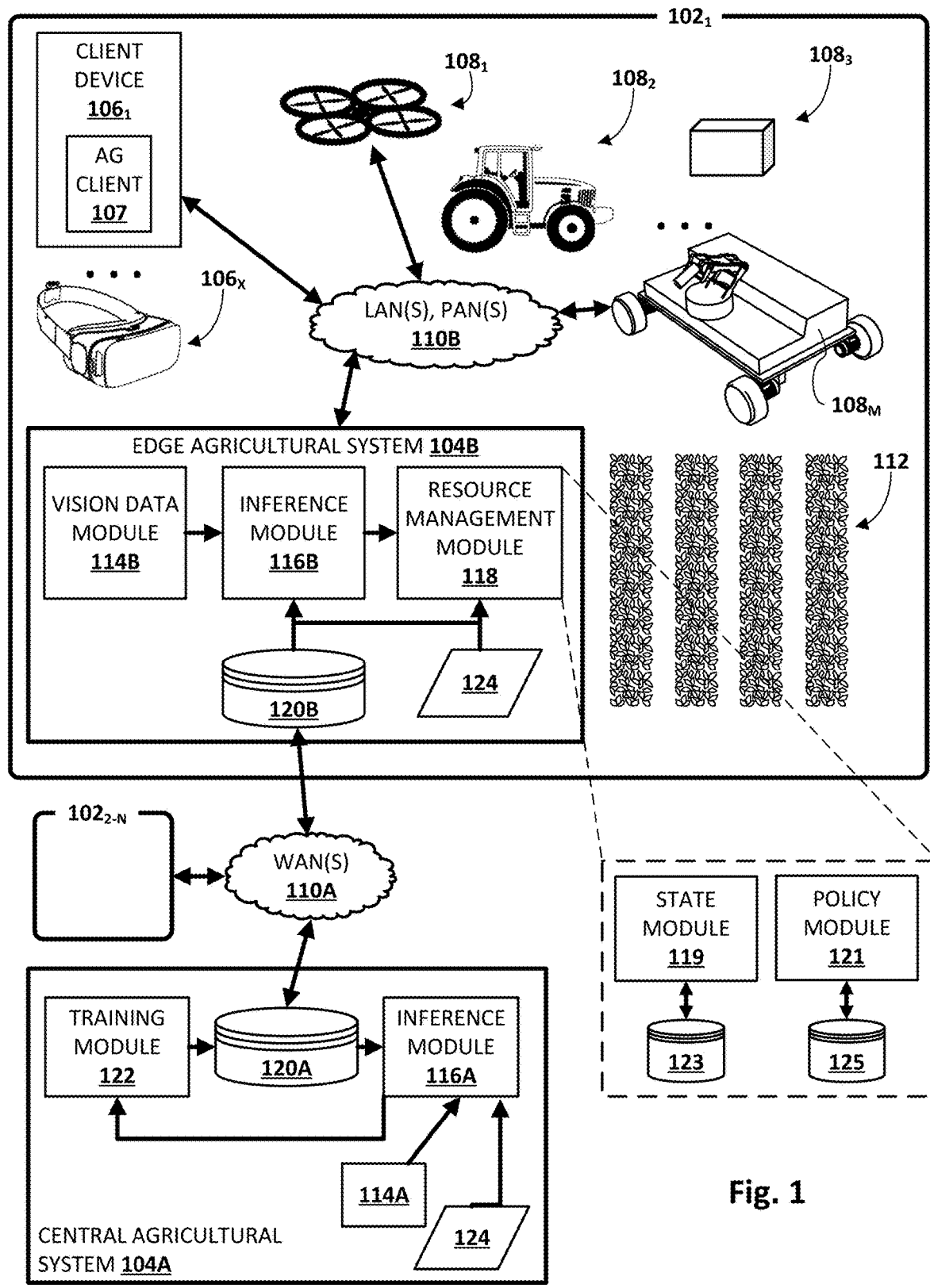
FIG. 1 schematically depicts an example environment in which disclosed techniques may be employed in accordance with various implementations.

Implementations are described herein for adaptively reallocating computing resources of resource-constrained devices between tasks performed in situ by those resource-constrained devices. Techniques described herein may optimize usage of computing resources by resource-constrained devices, enabling those resource-constrained devices to operate for longer periods of time and/or cover larger areas without needing to be recharged or otherwise serviced. For example, techniques described herein may ensure that a modular computing node or robot is able to be transported through an entire field before it requires a recharge. As used herein, a "resource-constrained device" may include, for instance, a battery-powered modular computing device that may or may not include integral sensors, a robot with one or more sensors, or any other device capable of transporting itself or being transported through an agricultural area while performing tasks.

Computing resources that are subject to reallocation may include, for instance, processor cycles, processor cores, memory (e.g., read-only memory or "ROM," random-access memory or "RAM," processor caches, registers, etc.), battery power, sensors and/or their capabilities/output, and/or various types of bandwidth. As used herein, "processor cycles" may refer to CPU cycles, GPU cycles, TPU cycles, etc. Bandwidth may include, for instance, network bandwidth (e.g., between a modular computing device or robot and a remote server), bus bandwidth (e.g., between sensors and processors), "inter-core" bandwidth between a plurality of processing cores, etc.

Computing resources may be directly or indirectly reallocated between tasks. An example of direct reallocation would be increasing or decreasing processor cycles, memory, or various types of bandwidth that are allocated/assigned to a task. Another example of direct reallocation would be to alter a sensor's memory buffer size, e.g., so that the freed memory can be allocated elsewhere. An example of indirect reallocation would be to increase or decrease a sensor's operational frequency or capture resolution, which in turn would influence an amount of computing resources (e.g., battery power, bandwidth(s), secondary memory such as local hard drive space, etc.) consumed by the sensor.

Computing resources may be reallocated between various types of tasks. Phenotypic tasks may include, for instance, detecting plant-parts-of-interest such as fruits, flowers, buds, etc., disease detection, weed detection, fruit count estimates, crop yield estimates, plant health inferences, detection of other phenotypic conditions (e.g., dehydration or over-hydration), and so forth. Computing resources may additionally or alternatively be reallocated between phenotypic tasks and other types of tasks, such as localization, mapping, robot self-maintenance, sensor calibration, memory cleanup, software updates, user interaction, user interface (UI) provision, etc.

In some implementations, resources may be allocated between tasks performed by a resource-constrained device based on a policy model. For example, the policy model may be used repeatedly throughout a plurality of iterations, in real time or near real time, to adaptively reallocate computing resources of resource-constrained devices between a plurality of tasks. Such a policy model may take various forms, such as a machine learning model or ensemble of machine learning models that are trained using techniques such as various types of reinforcement learning (e.g., Q-learning, Monte Carlo, Deep Q network, etc.).

In some such implementations, during each iteration, a current state of the resource-constrained device and/or its environment may be generated from various data sources, such as processes that monitor computing resource usage, environmental sensors, phenotypic inferences generated using machine learning models onboard the resource-constrained device, and/or other data sources such as climate databases, financial updates, etc. This state may be processed using the policy module to generate a probability distribution over a plurality of candidate reallocation actions. Based on this probability distribution, one or more of the candidate reallocation actions may be selected and performed. This process may repeat during each iteration, such that the resource-constrained device continuously adapts its resource usage to achieve various goals, such as making it all the way through a field without needing to be serviced, or continuing to provide one or more agricultural inferences specifically requested by agricultural personnel while also taking on new tasks as needed or warranted.

In various implementations, these goals or other similar data points may be used as rewards to continue to train the policy. For example, one or more short-term rewards may be provided during each iteration where use of one or more computing resources is decreased from a previous iteration. A longer-term reward may be making it all the way through a field without needing to be recharged. In some implementations, such a long-term reward may be distributed across multiple training iterations of the policy, e.g., with the reward being weighed more heavily during later iterations than earlier iterations. Other rewards may not be tied directly to resource usage. For example, there may be tasks that are particularly high-priority to a farmer—it may even be the case that the farmer would prefer these tasks be performed properly at the expense of less than an entire field being analyzed. In such a scenario, a reward may turn on a quality of inferences (e.g., measured by a confidence associated with each inference) during each iteration of the policy, and/or based on a quality of a cumulative inference drawn over multiple iterations.

In some implementations, phenotypic outputs generated by one or more phenotypic tasks may be monitored and used to make decisions about how or whether to reallocate computing resources. For example, these phenotypic outputs may be used to assemble the aforementioned state, which in turn is processed based on the policy to select and perform or more reallocation actions. Phenotypic outputs may include, for instance, inferences or predictions about plants generated using various techniques, such as machine learning models.

As one non-limiting example, suppose a general-purpose plant disease detection task is performed using a general-purpose convolutional neural network (CNN) that is trained to generate a plurality of probabilities indicative of presence or absence of a corresponding plurality of plant diseases. Should one or more of these probabilities exceed some threshold, indicating presence of a target disease, the resource-constrained device may reallocate computing resource(s) from some task (e.g., the general purpose disease detection task or another task) to a specialized phenotypic task for the target disease. For example, the specialized phenotypic task may apply a machine learning model that is specifically trained to annotate the target plant disease in images of plants, as opposed to simply generate a probability of presence/absence of that disease. Additional processor cycles, memory, or bandwidth may be directly reallocated to the specialized phenotypic task. Additionally or alternatively, a resolution or framerate of a vision sensor used by the specialized phenotypic task may be increased so that the disease can be annotated more accurately.

Farmers or other agricultural personnel may deploy resource-constrained devices into the field with expectations that specific agricultural/phenotypic tasks will be performed. However, it may become clear from output of various phenotypic tasks that other phenotypic tasks need to be performed as well. For example, it may become clear once a robot is in the field that many crops are infested with pests or disease. Yet, reallocating resources to these other tasks may be to the detriment of those agricultural tasks the farmer expects will be performed. Accordingly, in some implementations, before computing resources are reallocated to different tasks, audible or visual output may be provided at a computing device operated by the farmer or other agricultural personnel. This output may convey an effect candidate reallocation action(s) will have on a particular task and/or may include a prompt seeking approval to perform one or more candidate reallocation actions. That way a farmer is not blindsided by a resource-constrained device that changes the tasks it performs in the field without the farmer's permission.

FIG. 1 schematically illustrates an environment in which one or more selected aspects of the present disclosure may be implemented, in accordance with various implementations. The example environment includes a plurality of edge sites $102_{1-N}$ (e.g., farms, fields, plots, or other areas in which crops are grown) and a central agricultural system 104A. Additionally, one or more of the edge sites 102, including at least edge site $102_1$, includes an edge agricultural system 104B, a plurality of client devices $106_{1-X}$, human-controlled and/or autonomous farm equipment $108_{1-M}$, and one or more fields 112 that are used to grow one or more crops. Field(s) 112 may be used to grow various types of crops that may produce plant parts of economic and/or nutritional interest. These crops may include but are not limited to everbearing crops such as strawberries, tomato plants, or any other everbearing or non-everbearing crops, such as soy beans, corn, lettuce, spinach, beans, cherries, nuts, cereal grains, berries, grapes, and so forth.

One edge site $102_1$ is depicted in detail in FIG. 1 for illustrative purposes. However, as demonstrated by additional edge sites $102_{2-N}$, there may be any number of edge sites 102 corresponding to any number of farms, fields, or other areas in which crops are grown, and for which agricultural inferences such as crop yield predictions may be of interest. Each edge site 102 may include the same or similar components as those depicted in FIG. 1 as part of edge site $102_1$.

In various implementations, components of edge sites $102_{1-N}$ and central agricultural system 104A collectively form a distributed computing network in which edge nodes (e.g., client device 106, edge agricultural system 104B, farm equipment 108) are in network communication with central agricultural system 104A via one or more networks, such as one or more wide area networks ("WANs") 110A. Components within edge site $102_1$, by contrast, may be relatively close to each other (e.g., part of the same farm or plurality of fields in a general area), and may be in communication with each other via one or more local area networks ("LANs", e.g., Wi-Fi, Ethernet, various mesh networks) and/or personal area networks ("PANs", e.g., Bluetooth), indicated generally at 110B.

An individual (which in the current context may also be referred to as a "user") may operate a client device 106 to interact with other components depicted in FIG. 1. Each client device 106 may be, for example, a desktop computing device, a laptop computing device, a tablet computing device, a mobile phone computing device, a computing device of a vehicle of the participant (e.g., an in-vehicle communications system, an in-vehicle entertainment system, an in-vehicle navigation system), a standalone interactive speaker (with or without a display), or a wearable apparatus that includes a computing device, such as a head-mounted display ("HMD") that provides an AR or VR immersive computing experience, a "smart" watch, and so forth. Additional and/or alternative client devices may be provided.

Central agricultural system 104A and edge agricultural system 104B (collectively referred to herein as "agricultural knowledge system 104") comprise an example of a distributed computing network in which the techniques described herein may be implemented. Each of client devices 106, agricultural knowledge system 104, and/or farm equipment 108 may include one or more memories for storage of data and software applications, one or more processors for accessing data and executing applications, and other components that facilitate communication over a network. The computational operations performed by client device 106, farm equipment 108, and/or agricultural knowledge system 104 may be distributed across multiple computer systems.

Each client device 106 (and in some implementation, some farm equipment 108), may operate a variety of different applications that may be used, for instance, to obtain and/or analyze various agricultural inferences (real time and delayed) generated using various techniques. For example, a first client device $106_1$ operates agricultural ("AG") client 107 (e.g., which may be standalone or part of another application, such as part of a web browser). Another client device $106_X$ may take the form of a HMD that is configured to render 2D and/or 3D data to a wearer as part of a VR immersive computing experience. For example, the wearer of client device $106_X$ may be presented with 3D point clouds or polygon meshes representing various aspects of objects of interest, such as fruits of crops, weeds, crop yield predictions, etc. The wearer may interact with the presented data, e.g., using HMD input techniques such as gaze directions, blinks, etc.

Individual pieces of farm equipment $108_{1-M}$ may take various forms. Some farm equipment 108 may be operated at least partially autonomously, and may include, for instance, an unmanned aerial vehicle $108_1$ that captures sensor data such as digital images from overhead field(s)

112. Other autonomous farm equipment (e.g., robots) may include a robot (not depicted) that is propelled along a wire, track, rail or other similar component that passes over and/or between crops, a wheeled robot $108_M$, or any other form of robot capable of being propelled or propelling itself past crops of interest. In some implementations, different autonomous farm equipment may have different roles, e.g., depending on their capabilities. For example, in some implementations, one or more robots may be designed to capture data, other robots may be designed to manipulate plants or perform physical agricultural tasks, and/or other robots may do both. Other farm equipment, such as a tractor $108_2$, may be autonomous, semi-autonomous, and/or human-driven. Any of farm equipment 108 may include various types of sensors, such as vision sensors (e.g., 2D digital cameras, 3D cameras, 2.5D cameras, infrared cameras), inertial measurement unit ("IMU") sensors, Global Positioning System ("GPS") sensors, X-ray sensors, moisture sensors, barometers (for local weather information), photodiodes (e.g., for sunlight), thermometers, etc.

Figure 2:
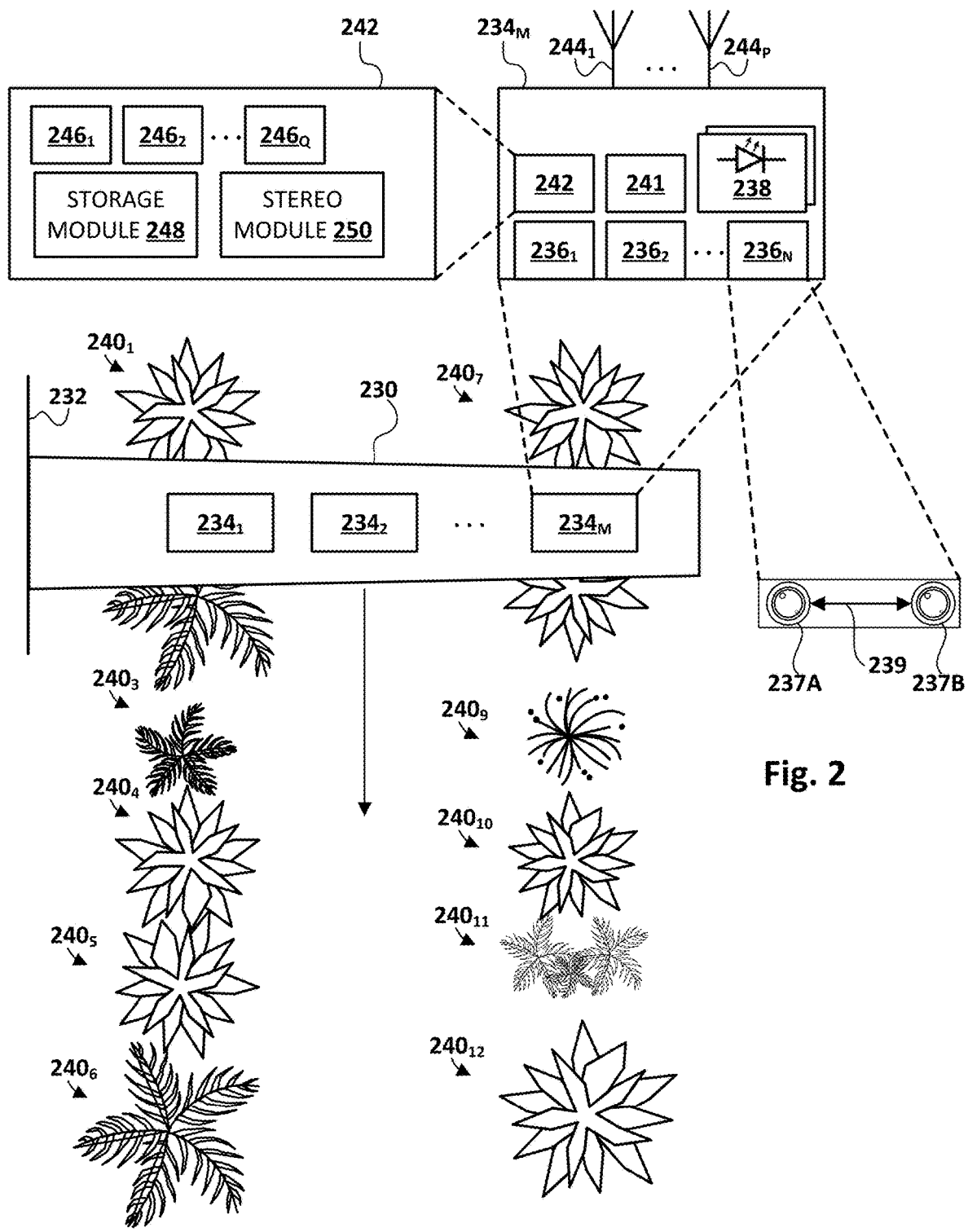
FIG. 2 depicts an example of how edge computing nodes configured with selected aspects of the present disclosure may be deployed in a field.

In some implementations, farm equipment 108 may take the form of one or more edge computing nodes $108_3$. An edge computing node $108_3$ may be a modular and/or portable data processing device and/or sensor package that may be carried through an agricultural field 112, e.g., by being mounted on another piece of farm equipment (e.g., on a boom affixed to tractor $108_2$ or to a truck) that is driven through field 112 and/or by being carried by agricultural personnel. In some cases, multiple edge computing nodes $108_3$ may be deployed on one farm vehicle or across multiple farm vehicles. Edge computing node $108_3$ may include logic such as processor(s), application-specific integrated circuits (ASICs), field-programmable gate arrays (FPGA), etc., configured with selected aspects of the present disclosure to capture and/or process various types of sensor data to adaptively reallocate computing resources. FIG. 2 schematically depicts one example of an edge computing node 234, and will be discussed in more detail shortly. Edge computing nodes $108_3$ and other edge-based farm equipment may be considered "resource-constrained" computing devices because, for instance, they lack sufficient memory and/or processor cycles to process all of the data they collect, they have limited battery power, their available internal and/or external data channels (e.g., busses, network connections) have limited bandwidth or throughput, etc.

In some examples, one or more of the components depicted as part of edge agricultural system 104B may be implemented in whole or in part on a single edge computing node $108_3$, across multiple edge computing nodes $108_3$ (e.g., mounted on the same tractor boom or irrigation pivot), and/or across other computing devices, such as client device(s) 106. Thus, when operations are described herein as being performed by/at edge agricultural system 104B, it should be understood that those operations may be performed by one or more edge computing nodes $108_3$, and/or may be performed by one or more other computing devices at the edge 102, such as on client device(s) 106.

In various implementations, edge agricultural system 104B may include a vision data module 114B, an edge inference module 116B, and a resource management module 118. Edge agricultural system 104B may also include one or more edge databases 120B for storing various data used by and/or generated by modules 114B, 116B, and 118, such as vision and/or other sensor data gathered by farm equipment $108_{1-M}$, agricultural inferences, machine learning models that are applied and/or trained using techniques described herein to generate agricultural inferences, and so forth. In some implementations one or more of modules 114B, 116B, and/or 118 may be omitted, combined, and/or implemented in a component that is separate from edge agricultural system 104B.

In various implementations, central agricultural system 104A may be implemented across one or more computing systems that may be referred to as the "cloud." Central agricultural system 104A may receive the massive sensor data generated by farm equipment $108_{1-M}$ (and/or farm equipment at other edge sites $102_{2-N}$) and process it using various techniques to make agricultural inferences. However, the agricultural inferences generated by central agricultural system 104A may be delayed (and are referred to herein as "delayed crop agricultural inferences"), e.g., by the time required to physically transport portable data devices (e.g., hard drives) from edge sites $102_{1-N}$ to central agricultural system 104A, and/or by the time required by central agricultural system 104A to computationally process this massive data.

In order to adaptively reallocate computing resources of resource-constrained edge devices (e.g., $108_3$) in real time or near real time based on agricultural inferences, those agricultural inferences may be needed more quickly than central agricultural system 104A is capable of providing them. Accordingly, edge agricultural system 104B at edge site $102_1$ may be configured to generate inferences in situ, at the edge, so that these inferences can be evaluated (also in situ) to determine in real time (or near real time) how to reallocate various computing resources of resource-constrained devices.

Nonetheless, the delayed agricultural inferences made by central agricultural system 104A may be used for a variety of purposes, not the least of which is to train the machine learning models used by edge inference module 116B to generate inferences that can then be evaluated, e.g., along with other information, to reallocate computing resources of resource-constrained devices in real time or near real time. For example, central agricultural system 104A may include a training module 122, a central inference module 116A (which may share some characteristics with edge inference module 116B), and a central database 120A that stores one or more machine learning models. Central agricultural system 104A in general, and training module 122 and/or central inference module 116A in particular, may be configured to train those machine learning models (before and/or throughout their deployment) to generate agricultural inferences that are used to make decisions about reallocating computing resources of resource-constrained devices. To perform this training, training module and central inference module 116A may utilize sensor data generated by farm equipment $108_{1-M}$, e.g., alone and/or in concert with other data 124.

In some implementations, edge agricultural system 104B is able to generate agricultural inferences in real time or near real time because edge inference module 116B may selectively process less than all the massive sensor data generated by farm equipment $108_{1-M}$. In other words, the data processed in real time or near real time by edge inference module 116B may have a level of detail that is lower than, for instance, level(s) of detail the sensor(s) are capable of generating or that the sensor(s) actually generate. For example, in some implementations, data may be sampled, e.g., by vision data module 114B from one or more vision sensors onboard one or more farm equipment $108_{1-M}$, at a frequency and/or resolution that is lower than the data actually generated by those vision sensor(s). Alternatively, the vision sensors themselves may be operated at lower frequencies and/or resolutions than they are capable of operating.

Whichever the case, the data may be applied, e.g., continuously and/or periodically by edge inference module 116B, as input across one or more machine learning models stored in edge database 120B to generate agricultural inferences that are indicative of, for instance, targeted plant trait(s) detected in/on one or more plants in the agricultural field 112. In some cases, one or more of these machine learning model(s) may be stored and/or applied directly on farm equipment 108, such as edge computing node $108_3$, to make an inference about plants within the agricultural field 112.

In some implementations, edge agricultural system 104B may selectively (e.g., on an "as needed" basis) download and/or install trained models that are stored in database 120A of central agricultural system 104A. For example, if edge inference module 116B determines, based on processing of vision data, that a particular plant trait is detected, edge agricultural system 104B may download new machine learning model(s) that are trained to make inferences related to that detected plant trait. As one example, inference module 116B may apply a machine learning model to vision data to detect, generically, the presence of plant disease, without detecting which specific plant disease(s) are present. On detection of potential disease, inference module 116B may request and/or download, from central agricultural system 104A, one or more machine learning models that are trained to detect specific types of plant disease. Edge inference module 116B may then apply these newly-obtained model(s) to the same vision data and/or to additional vision data (e.g., gathered further along the path of the vehicle, or from a prior location after the vehicle reverses course) to determine which specific plant diseases are present.

In contrast to edge agricultural inference system 104B, central inference module 116A may have the virtually limitless resources of the cloud at its disposal. Accordingly, central inference module 116A may apply all of the sensor data generated by farm equipment $108_{1-M}$ as input across machine learning model(s) stored in central database 120A to generate the delayed agricultural inferences described previously. And in some implementations, training module 122 may train the machine learning model(s) stored in database 120A based on a comparison of these delayed agricultural inferences to ground truth data (e.g., realized crop yields, human-observed disease or blight). Based on such a comparison, training module 122 may employ techniques such as back propagation, gradient descent, etc., to update the machine learning model(s) stored in central database 120A. The updated machine learning model(s) may subsequently be used by both edge inference module 116B and central inference module 116A to generate, respectively, real time and delayed agricultural inferences. In some implementations, edge agricultural inference system 104B may participate and/or contribute to training of machine learning models, e.g., by way of techniques such as federated learning. For example, edge agricultural inference system 104B may generate a local gradient that can then be incorporated into a central machine learning model along with other local gradients generated at other edge sites.

In some implementations, one or more components of edge agricultural system 104B, such as vision data module 114B and/or edge inference module 116B, may effectively deallocate computing resources by processing a subset of high spatial/temporal/spectral resolution data to generate one or more image embeddings (or vectors). In some such implementations, this processing may include applying the subset of high resolution digital images as input across at least a portion of a machine learning module such as a CNN to generate the image embeddings/vectors. Using image embeddings may be more efficient than, for instance, counting individual crops, which may require 3D reconstruction from a point cloud, object tracking, etc. With image embeddings, it is possible to estimate the density of plant parts of interest (e.g., strawberries), rather than counting individual plant parts of interest. Density of plant parts of interest may be measured per plant, per meter, etc.

As noted previously, various types of machine learning models may be applied by inference modules 116A/B to generate various agricultural inferences and/or phenotypical output. Additionally, various types of machine learning models may be used to generate image embeddings that are applied as input across the various machine learning models. These various models may include, but are not limited to, RNNs, LSTM networks (including bidirectional), transformer networks, feed-forward neural networks, CNNs, support vector machines, random forests, decision trees, etc.

Additionally, other data 124 may be applied as input across these models besides sensor data or embeddings generated therefrom. Other data 124 may include, but is not limited to, historical data, weather data (obtained from sources other than local weather sensors), data about chemicals and/or nutrients applied to crops and/or soil, pest data, crop cycle data, previous crop yields, farming techniques employed, and so forth. Weather data may be obtained from various sources other than sensor(s) of farm equipment 108, such as regional/county weather stations, etc. In implementations in which local weather and/or local weather sensors are not available, weather data may be extrapolated from other areas for which weather data is available, and which are known to experience similar weather patterns (e.g., from the next county, neighboring farms, neighboring fields, etc.). Alternatively, weather data may be predicted from other variables or features within the agricultural area.

In this specification, the term "database" and "index" will be used broadly to refer to any collection of data. The data of the database and/or the index does not need to be structured in any particular way and it can be stored on storage devices in one or more geographic locations. Thus, for example, database(s) 120A and 120B may include multiple collections of data, each of which may be organized and accessed differently.

Resource management module 118 may be configured to reallocate computing resources of resource-constrained devices in situ (e.g., while the agricultural vehicle carrying the resource-constrained device moves through agricultural field 112) in real time or near real time based at least in part on inferences drawn generated by edge inference module 116B. As indicated by the arrows in FIG. 1, in some implementations, resource management module 118 may utilize machine learning model(s) stored in edge database 120B and/or other data 124 to determine whether and how to adjust agricultural equipment parameters.

In some implementations, resource management module 118 may include a state module 119 and a policy module 121. In other implementations, state module 119 and policy module 121 may be combined, and/or one or the other may be omitted. State module 119 may be configured to evaluate various information and assemble a state based on that information. The information used by state module 119 may come from various sources. One source is inferences generated by edge inference module 116B. For example, state module 119 may generate a state that includes data indicative of visual annotations (e.g., bounding shapes, key points, pixel-wise annotations) of plant-parts-of-interest. This data may include, for instance, statistics about the visual annotations (e.g., average size, spatial distribution, etc.), the visual annotations themselves and/or the underlying vision data they annotate, and so forth. Other sources of data for state module 119 may include, for instance, the other data 124 mentioned previously, or monitored computing resource data. For example, resource management module 118 or another component may monitor battery power, memory usage (e.g., RAM and/or longer term memory), processor cycle status (e.g., percentage used, temperature, throughput, etc.), available bandwidth between components of the resource-constrained device and/or between the resource-constrained device and outside computing devices, and so forth.

In some implementations, to assemble a state, state module 119 may rely on machine learning model(s) stored in a database 123, which may or may not be part of edge database 120B. These machine learning model(s) may include, for instance, machine learning models that are trained to generate, as a state, semantically-rich embeddings. Such a semantically-rich embedding may capture various information, such as the visual annotations mentioned previously, other inferences generated by edge inference module 116B (e.g., classifications, predictions, etc.), and any of the other data mentioned previously that is available to or accessible by resource management module 118.

Policy module 121 may be configured to apply a policy, such as a machine learning model 125 that is trained using various types of reinforcement learning, to the state generated by state module 119 to generate a probability distribution over an action space. Such an action space may include, for instance, a plurality of candidate actions for reallocating computing resources of a resource-constrained device (e.g., $108_3$). Policy module 121 may select, and cause to be performed, one or more actions based on that probability distribution. In some implementations, policy module 121 may select the n (positive integer) candidate actions having the greatest probabilities or probabilities that exceed some threshold (e.g., a static threshold, standard deviation, etc.).

FIG. 2 depicts an example field of plants $240_{1-12}$. A boom 230 mounted to a vehicle 232 (mostly not visible in FIG. 2, e.g., a tractor, a robot, a truck, etc.) is being carried over plants $240_{1-12}$ as shown by the arrow to gather sensor data. Boom 230 may include, for instance, sprinklers for irrigation, sprayers for chemical application, etc. Also mounted on boom 230 are a plurality of edge computing nodes $234_{1-M}$ (which may share characteristics with edge computing node $108_3$ in FIG. 1) that are configured with selected aspects of the present disclosure. Although shown as boxes on top of boom 230 in FIG. 2, edge computing nodes $234_{1-M}$ may alternatively be mounted at other locations of boom 230, such as on its sides or bottom. And while multiple edge computing nodes $234_{1-M}$ are depicted in FIG. 2, any number of edge computing nodes 234, such as a single edge computing node 234, may be deployed in similar fashions.

As shown by the called-out window at top right, edge computing node $234_M$ includes one or more sensors in the form of vision sensors $236_{1-N}$, one or more lights 238, a light controller 241, and logic 242 that is configured to carry out selected aspects of the present disclosure. Other edge computing nodes may or may not be similarly configured. Vision sensors $236_{1-N}$ may take various forms, and may or may not be the same as each other. These forms may include, for instance, an RGB digital camera, an infrared camera, a 2.5D camera, a 3D camera, and so forth. For example, vision sensor $236_N$ takes the form of a stereoscopic camera with two lenses 237A, 237B separated by an interaxial distance 239. One or more of these 2D vision sensors $236_{1-N}$ may capture images at various framerates (frames per second, or "FPS"), such as 30 FPS. In some implementations in which one or more of vision sensors $236_{1-N}$ captures 2.5D or 3D data, a point cloud having a resolution of, for instance, 640 px×480 px and/or a framerate of 10 FPS or greater may be implemented. In some implementations, vision sensor(s) 236 may capture 2D data and then generate 3D data (e.g., point clouds) using techniques such as structure from motion (SFM), stereo reconstruction, or dense optical flow 3D reconstruction, to name a few. In some implementations, one or more of vision sensors $236_{1-N}$ may be configured to capture vision data in a variety of different wavelengths, including but not limited to RGB, infrared, grayscale, X-ray, and so forth.

Light(s) 238 and light controller 241 may be configured to illuminate plants 240, e.g., in synch with operation of vision sensors $236_{1-N}$, in order to insure that the vision data that is captured is illuminated sufficiently so that it can be used to make accurate agricultural inferences. Light(s) 238 may take various forms, such as the light emitting diode (LED) depicted in FIG. 2, halogen lamps, incandescent lamps, infrared lamps, black lights, etc. In various implementations, light(s) 238 may be operated, e.g., by light controller 241, to emit various amounts and/or strengths of light (or more generally, electromagnetic radiation). For example, in some implementations, light(s) 238 may emit 14,000 lux of luminance or greater. In some such implementations, light controller 241 may also trigger vision sensors $236_{1-N}$ to acquire image data in sync with activation of light(s) 238.

Edge computing node $234_M$ also includes one or more wireless antenna $244_{1-P}$. In some implementations, each wireless antenna 244 may be configured to transmit and/or receive different types of wireless data. For example, a first antenna $244_1$ may be configured to transmit and/or receive Global Navigation Satellite System (GNSS) wireless data, e.g., for purposes such as localization and/or ROI establishment. Another antenna $244_P$ may be configured to transmit and/or receive IEEE 802.12 family of protocols (Wi-Fi) or Long-Term Evolution (LTE) data. Another antenna 244 may be configured to transmit and/or receive 5G data. Any number of antennas 244 may be provided to accommodate any number of wireless technologies.

In some implementations, an edge computing node 234 may be capable of localizing itself within agricultural field 112 using various technologies. For example, the GNSS antenna $244_1$ may interact with satellite(s) to obtain a position coordinate. Additionally or alternatively, edge computing node 234 may use techniques such as inertial measurement units (IMU) that are generated by, for instance, sensor(s) integral with wheels (not depicted) of vehicle 232, accelerometer(s), gyroscope(s), magnetometer(s), etc. In yet other implementations, wireless triangulation may be employed. In some implementations, edge computing node 234 may be capable of localizing itself with an accuracy of 20 cm or less, e.g., at a frequency of 10 Hz or greater (or an IMU frequency of 100 Hz or greater).

Logic 242 may include various types of circuitry (e.g., processor(s), FPGA, ASIC) that is configured to carry out selected aspects of the present disclosure. For example, and as shown in the called-out window at top left in FIG. 2, logic 242 may include any number of tensor processing units (TPU) $246_{1-Q}$, a storage module 248, and a stereo module 250 (one or more graphical process units (GPU) and/or central processing units (CPU) may also be present, even if not depicted). In some implementations, four TPUs $246_{1-4}$ may be employed to process sensor data, e.g., in parallel, using four different machine learning models, e.g., at an inference framerate per model of 20 FPS or greater.

Other configurations are possible. For example, instead of some number of TPUs, in some examples, an edge computing node 234 may include some number of GPUs, each with some number of cores. With the example operational parameters of edge computing node 234 described herein, in some examples, edge computing node 234 may be capable of being moved (or moving itself) at various speeds to perform its tasks, such as up to 12 m/s.

Storage module 248 may be configured to acquire and store, e.g., in various types of memories onboard edge computing node 234, sensor data acquired from one or more sensors (e.g., vision sensors $236_{1-N}$). In order to accommodate sensor input streams of, for instance, 1 GB/s, storage module 248 may, in some cases, initially write sensor data to a dedicated logical partition on a Non-Volatile Memory Express (NVMe) drive. Subsequently, e.g., after processing by inference module 116B, the sampled data may be copied to a Redundant Array of Inexpensive Disks (RAID) solid state drive for long-term storage. Stereo module 250 may be provided in some implementations in order to reconcile images captured by 2D vision sensors that are slightly offset from each other, and/or to generate 3D images and/or images with depth.

Figure 3:
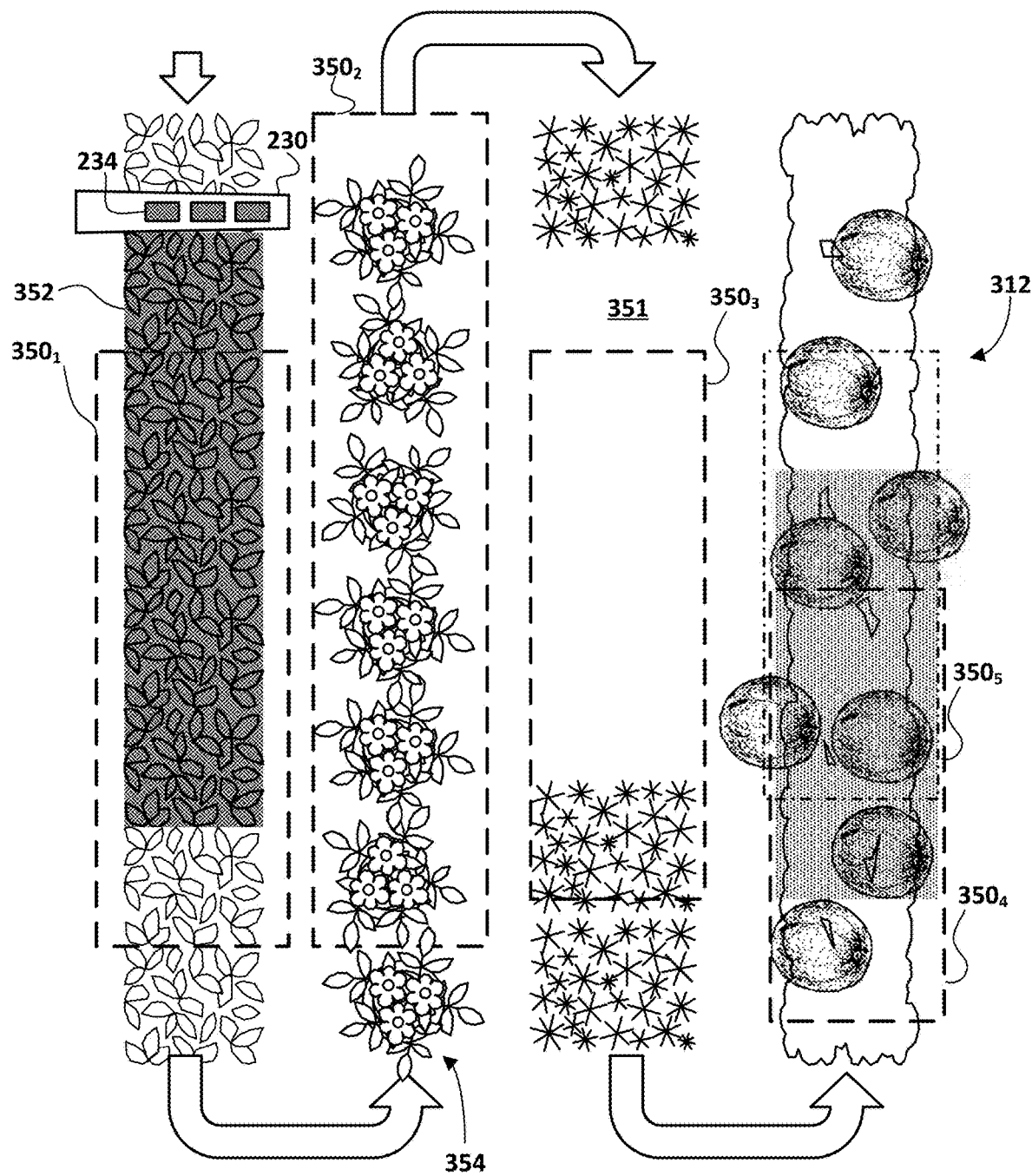
FIG. 3 schematically depicts examples of how techniques described herein may be implemented by an edge computing device to adaptively reallocate computing resources of resource constrained devices in situ.

FIG. 3 demonstrates an example of how techniques described herein may be performed to adaptively reallocate computing resources of resource-constrained devices in situ, e.g., in a particular field 312. In FIG. 3, a plurality of edge computing nodes 234 are mounted on a boom 230 of a farm vehicle (not depicted). In FIG. 3, the farm vehicle is traveling such that boom 230 and edge computing nodes 234 are carried over four (vertical in FIG. 3) rows of plants. However, this is not meant to be limiting, and disclosed techniques may be performed with other types of agricultural equipment, such as agricultural robots, UAVs, etc.

Starting at top left, boom 230 (with three edge computing nodes onboard as indicated by the shaded rectangles) may be carried through field 312 along the trajectory shown by the arrows. Thus, boom 230 is first carried over the leftmost row from top to bottom, then is turned around and carried over the second row from bottom to top. Boom 230 is then turned around again and carried down over the third row, and once again is turned around and brought up over the fourth (right-most row). To accomplish this, the farm vehicle (not depicted) to which boom 230 is attached may be traversed between the various rows.

The left-most row includes a first kind of plant, e.g., some variety of oats. As indicated by the shading, at position 352 of the left-most row, a plant disease is detected. For example, starting at position 352, the oats may be infected with crown rust. When boom 230 passes over position 352, edge inference module 116B may process the vision data captured by vision sensor(s) to generate an inference that suggests the presence of crown rust. This inference may be confirmed, corroborated, refuted, etc., based on other data, such as recent environmental conditions, etc.

Based on the inference(s) and any other applicable data, computing resources may be reallocated to a particular task, such as a task configured to monitor specifically for crown rust. If no crown rust monitoring task is yet operating, one may be initiated and resources may be reallocated to it, e.g., from another process. These computing resources may include, for instance, extra memory that can be used to store higher-resolution imagery that is captured while crown rust is evident. Additionally or alternatively, these resources may include sensors and/or settings thereof, such as parameter(s) of vision sensor(s) 236 and/or light source(s) 238.

As an example, light source(s) 238 may be transitioned to emit light at a greater intensity and/or different wavelength (e.g., infrared), which may require more power. In some scenarios, these computing resources may be deallocated from other tasks in order to make up for the increased power usage required by the different light setting. For example, another task may be deprioritized (at least temporarily) to receive a smaller fraction of processor cycles, thereby drawing less power. However, this tradeoff may be worthwhile assuming there remains sufficient battery power to perform other tasks and/or to accomplish various goals, such as capturing sensor data of an entire field.

In FIG. 3, a first region of interest (ROI) $350_1$ is depicted that shows where edge computing node 234 makes adjustments (at the top of first ROI $350_1$) to better capture this potential crown rust, as well as where those adjustments end (at the bottom edge of first ROI $350_1$), e.g., in response to some exit condition. As indicated by the lack of shading, the bottom plant within first ROI $350_1$ is not infected with crown rust. In response to such an exit condition, the temporary computing resource reallocations may be undone, e.g., by policy module 121, for the remainder of the left-most row. Exit conditions may take various forms and may be configured, for instance, by agricultural personnel. In the example of FIG. 3, the exit condition illustrated by first ROI $350_1$ is detection of some number of consecutive instances of uninfected plants. Other exit conditions are contemplated.

Boom 230 is then carried over the second-from-left row, upward along the page. In this row, a second ROI $350_2$ is established upon detection of a particular type of flowering plant 354. Second ROI $350_2$ may be tied off when, for instance, some number of consecutive instances of plants other than the flowering plant are detected, or at the end of the second-from-left row as depicted in FIG. 3. These flowering plants may have physical characteristics such as height, width, color, or other phenotypic traits that are best inferred, for instance, using particular machine learning models (e.g., a CNN trained to annotate the flowers or parts thereof). Accordingly, state module 119 may generate and/or assemble a state that suggests presence of these flowering plants based on various inferences drawn from vision data that captures the bottom plant in the second—from left row in FIG. 2. As a consequence, policy module 121 may reallocate various computing resources to an existing task or new task that processes vision data using the CNN trained to detect trait(s) of the particular flowing plant. If necessary, edge inference module 116B operating on an edge computing node 234 may download, e.g., from central agricultural system 104A in real time, the machine learning models (e.g., CNN(s)) that are trained to detect various traits of the particular type of flowering plant.

In the third—from left row (traveling downward on the page), another ROI $350_3$ is established. Third ROI $350_3$ may be established based on detecting bare ground 351, as opposed to plants. Tasks such as fruit or disease detection may become less relevant while a vision sensor passes over bare ground. On the other hand, tasks such as soil analysis and/or tillage practice monitoring may become increasingly relevant. Accordingly, upon detecting bare ground 351 just above third ROI $350_3$, state module 119 may generate a state that indicates, among other things, the presence of bare ground as opposed to plants. Consequently, policy module 121 may reallocate various computing resources from tasks configured to detect phenotypic traits to task(s) configured to make inferences about bare ground, such as tillage practices, soil composition, soil moisture, and so forth. This may continue, for instance, within third ROI $350_3$ until vegetation is once again detected, at which point policy module 121 may reallocate computing resources back to phenotypic tasks. It may be the case that overall computing resource usage may decrease as a result of third ROI $350_3$. This may be beneficial for extending battery life, especially if unforeseen circumstances emerge later in the field.

In the right-most row (traveling upward on the page), a new type of plants (e.g., melons) is planted within ROI $350_4$. Melons are relatively large compared to other plant-parts-of-interest such as berries or peapods, for instance. Thus, phenotypic tasks for detecting traits of melons may not require as many computing resources as other phenotypic tasks. For example, vision data used for melon detection may not need to be captured at as high a resolution or framerate as vision data used for other phenotypic tasks. In some implementations, based on this knowledge, policy module 121 may adaptively reallocate computing resources by decreasing parameters associated with vision sensors, such as resolution, framerate, synchronized lighting, memory, processor cycles dedicated to preprocessing the vision data, etc.

However, as indicated by the shading, while traveling across the right-most row, at least a region of the row is subject to a different ambient light condition. For example, a cloud may be overhead while boom 230 passes over that region of the right-most row. Or perhaps there is a nearby structure or tree that casts a shadow on that region. Whichever the case, the ambient light condition is altered in that region, which may influence not only the quality of images captured in that area, but the quality of inferences generated by edge inference module 116B based on those inferences.

Accordingly, in various implementations, a fifth ROI $350_5$ (shown in dash-dot-dash line) may be established, e.g., upon detection of the change in ambient light from images captured in the shaded portion outside of and beneath fourth ROI $350_4$. For example, a confidence associated with inferences generated by edge inference module 116B may decrease suddenly upon entering the shaded region. This may trigger state module 119 to generate a state that reflects this low confidence. This state may cause policy module 121 to reallocate computing resources accordingly. These reallocations may include, for instance, turning on one or more light sources 238, increasing a brightness of one or more light sources, altering an exposure time of one or more vision sensors 236, etc.

Figure 4:
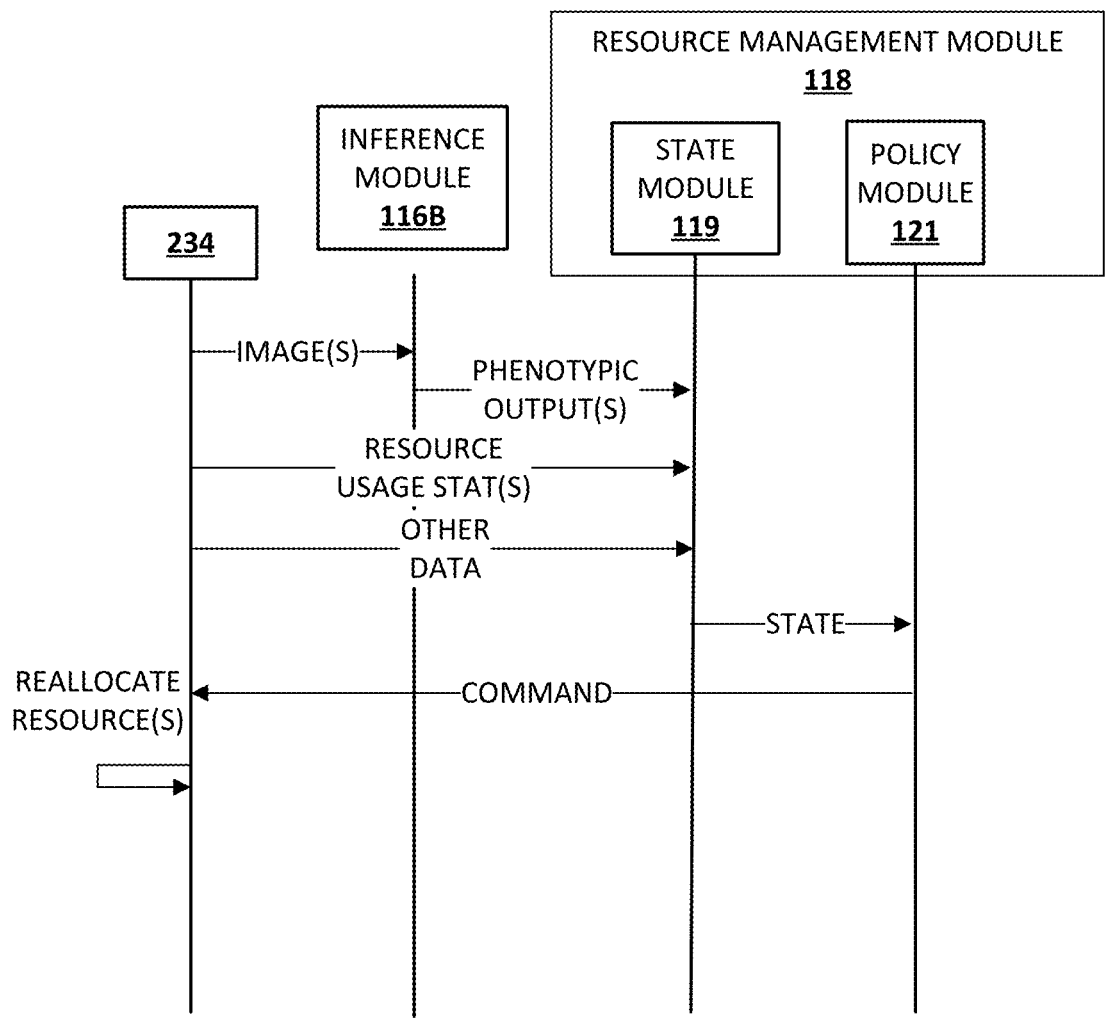
FIG. 4 schematically depicts an example of how various components described herein may exchange and process data to adaptively reallocate computing resources of resource-constrained devices, such as edge-based agricultural equipment.

FIG. 4 depicts an example of how various components may cooperate to implement aspects of the present disclosure. In a first example starting at top, images captured by vision sensor(s) (not depicted in FIG. 4) are provided by edge computing node 234 to edge inference module 116B, e.g., by way of vision data module 114B (not depicted in FIG. 4). Edge inference module 116B may process those images, e.g., using one or more machine learning models or other techniques (e.g., rules-based), to generate one or more phenotypic outputs, which are provided to state module 119 of resource management module 118.

Edge computing node 234 may also provide resource usage information to state module 119. These resource usage information may include, for instance, processor cycle statistics, memory statistics, available battery power, network connection quality and/or availability, etc. Edge computing node 234 may additionally or alternatively provide other data as well. This other data may or may not correspond to other data 124 in FIG. 4. Additionally or alternatively, this other data may include information about the tasks (phenotypic and otherwise) being performed by edge computing node 234, such as which tasks have which priority, which tasks may be expendable, which tasks are mission-critical, etc.

Based on these data, state module 119 may generate, and provide to policy module 121, a state. For example, state module 119 may generate one or more embeddings that encode these various data in various ways. Based on the state, policy module 121 may generate and issue one or more commands to edge computing node 234. Based on these commands, edge computing node 234 may adaptively reallocate various computing resources.

Figure 5:
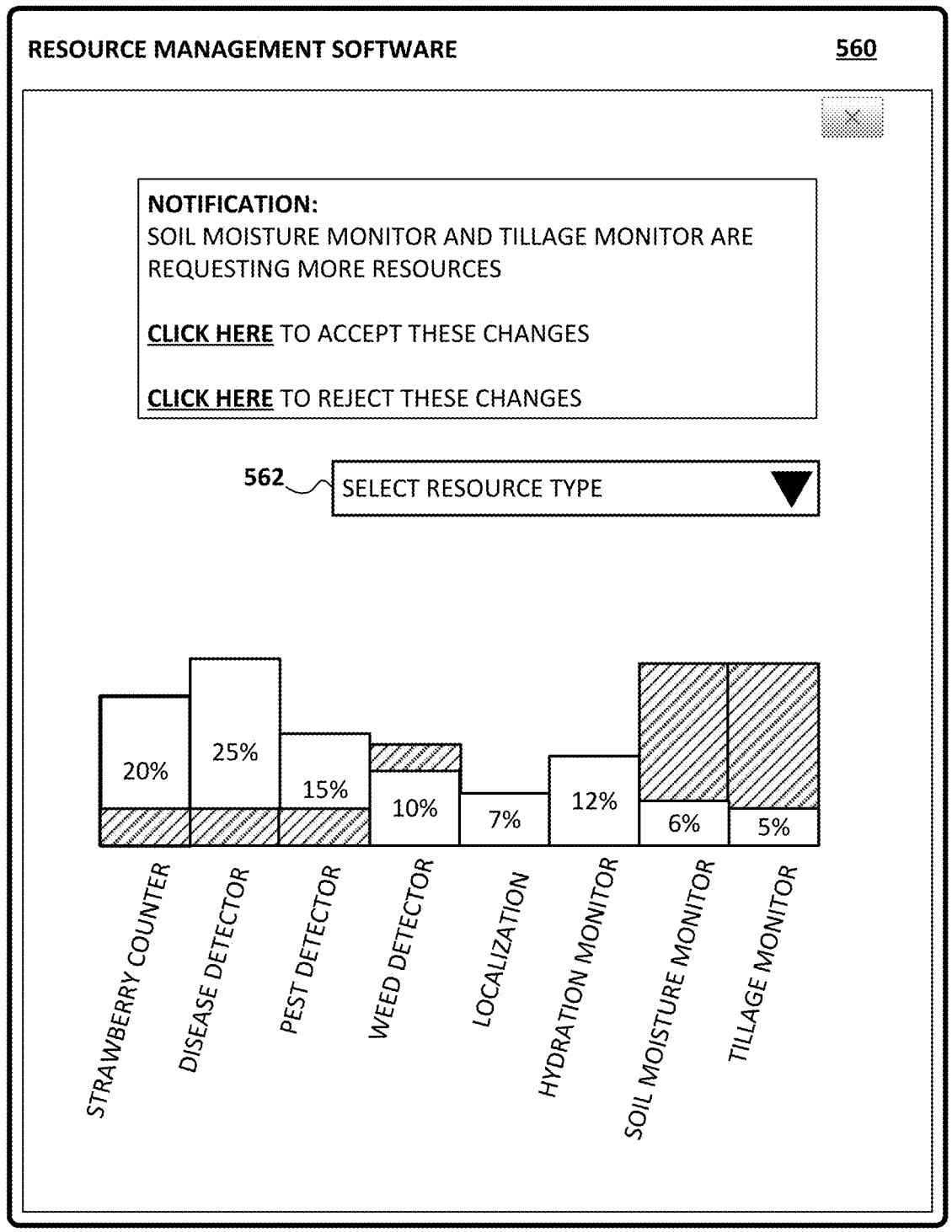
FIG. 5 schematically depicts an example graphical user interface (GUI) configured with selected aspects of the present disclosure.

FIG. 5 schematically depicts an example graphical user interface (GUI) 560 configured with selected aspects of the present disclosure as part of a resource management software module. GUI 560 may be presented, for instance, on a client device 106 so that agricultural personnel may be able to monitor how computing resources are allocated and reallocated using techniques described herein. As shown in the bar chart at bottom, a number of tasks, phenotypic and otherwise, are being performed by an edge computing resource, such as an edge computing node 234. These phenotypic tasks may include, for instance, a strawberry counter, a disease detector, a pest detector, a weed detector, a hydration monitor, a soil moisture monitor, and a tillage monitor. A localization (and mapping where applicable) routine is one non-limiting example of a non-phenotypic task—others are contemplated.

Each of the tasks represented in the bar chart in FIG. 5 may currently be allocated some percentage of some computing resource, such as RAM, processor cycles, various types of bandwidth, use of all or part of a sensor array, etc. A selectable element 562 such as a drop down menu may be provided in some implementations to select which computing resource allocation to view. In addition, in some implementations, multiple different allocations of multiple different computing resources may be combined to generate a total or aggregate computing resource usage or score that conveys, at a high level, how much computing resources are currently allocated to individual tasks.

In this example, a notification has been provided to a user indicating that the soil moisture monitor and tillage monitor are requesting more resources. This may be because, for instance, an area of bare ground (e.g., 351 in FIG. 3) has been encountered, making these tasks perhaps more immediately relevant than other tasks, such as the strawberry counter. In some implementations, the user may be prompted to approve or deny the reallocation of these computing resources.

Additionally or alternatively, in some implementation, the user may be apprised of not only the effect of the reallocations on these two tasks, but on other tasks as well. For example, and as indicated by the shaded bars in FIG. 5, the increase in computing resources allocated to the soil moisture and tillage monitoring tasks may cause a corresponding reduction or deallocation of computing resources from other tasks. For instance, the strawberry counter, disease detector, and pest detector tasks currently are using 20%, 25%, and 15% of one or more computing resources. If the proposed reallocations are accepted by the user, then those allocations decrease considerably, whereas the computing resources allocated to the soil moisture and tillage monitoring tasks increase considerably. In some implementations, resources allocated to the weed detector task may also increase, e.g., if the farmer wants to prevent weeds from taking over bare ground. Other tasks, such as a localization task, may or may not have computing resources reallocated.

Figure 6:
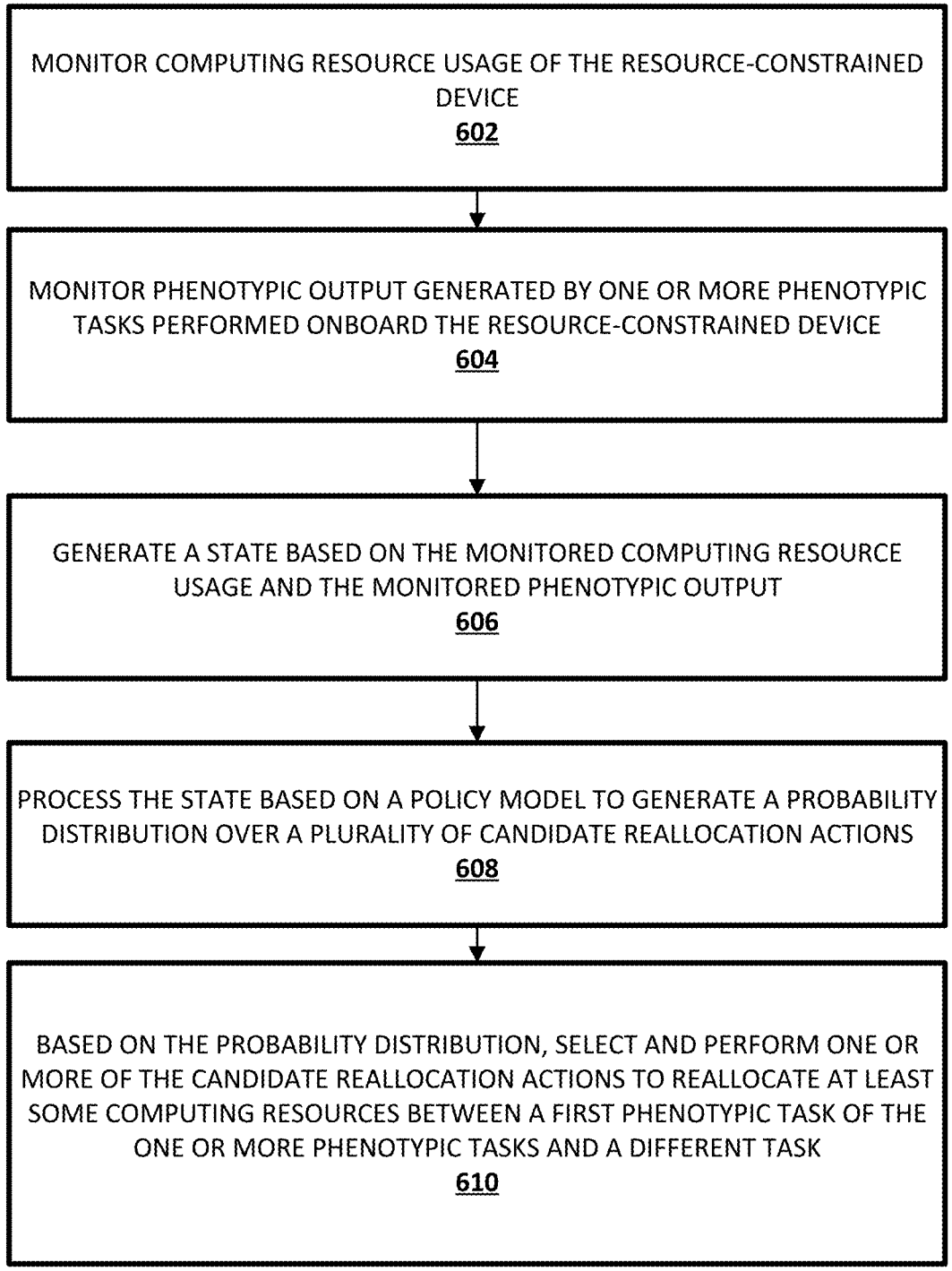
FIG. 6 is a flowchart of an example method in accordance with various implementations described herein.

FIG. 6 illustrates a flowchart of an example method 600 implemented by a resource-constrained device while the resource-constrained device is transported through an agricultural area. Method 600 may be implemented using one or more resource-constrained edge processors (e.g., logic 242 of edge computing node $108_3/234$ that implements edge agricultural system 104B) at an edge of a distributed computing network that are remote from one or more central servers (e.g., that implement central agricultural system 104A) of the distributed computing network. For convenience, operations of method 600 will be described as being performed by a system configured with selected aspects of the present disclosure. Other implementations may include additional operations than those illustrated in FIG. 6, may perform operation(s) of FIG. 6 in a different order and/or in parallel, and/or may omit one or more of the operations of FIG. 6.

At block 602, the system, e.g., by way of resource management module 118, may monitor computing resource usage of the resource-constrained device. For example, various statistics about how various computing resources are allocated among a plurality of tasks, such as processor cycles, memory, bandwidth(s), etc., may be captured.

At block 604, the system, e.g., by way of resource management module 118, may monitor phenotypic output generated by one or more phenotypic tasks performed onboard the resource-constrained device. As an example, one or more monitored phenotypic outputs may signal potential presence of one or more phenotypic conditions, such as plant disease, pest presence, plant dehydration, etc. Detection of such a condition may be captured in a state generated by state module 119 at block 606, which in turn may cause policy module 121 to reallocate computing resources to a task that, for instance, applies a machine learning model trained to detect presence of the phenotypic condition. Other phenotypic outputs may include, for instance, various plant traits, sizes of plant-parts-of-interest, health of various plant parts (e.g., leaves, flowers, fruit, stems, etc.), overall plant sizes or other spatial dimensions of plants, color of one or more plant parts, etc.

As alluded to above, at block 606, the system, e.g., by way of state module 119, may generate a state based on the monitored computing resource usage and the monitored phenotypic output. In some implementations, this state may include one or more embeddings that encode the various monitored data. In some implementations, this state may include an embedding generated from vision data and/or annotations of vision data, such as bounding boxes, key points, pixel-wise annotations, etc. In some such implementations, the embedding (or more generally, the state) may include statistics about and/or derived from such annotations, such as spatial distribution of key points (e.g., how densely distributed is a particular plant-part-of-interest such as a pea pod), average/median sizes of bounding boxes, overall fruit volume estimations, etc.

In some implementations, state module 119 may generate the state based on an amount of battery power required for the resource-constrained to achieve one or more goals. These one or more goals may include, for instance, performance of the one or more phenotypic tasks over at least a threshold amount of an agricultural area such as a field. For example, a farmer's highest priority may be to collect particular types of data and/or generate particular agricultural inferences over an entire field. By incorporating the remaining battery power into the state at each iteration (e.g., along with an indication of the farmer's goal), policy module 121 may generate probability distributions that are more likely to result in the farmer's goals being met, even at the expense of some perhaps lesser or latent goals (e.g., detecting some pest that the farmer didn't anticipate).

In some implementations, state module 119 may generate the state based on one or more environmental conditions of the agricultural area. One example was described above with reference to FIG. 4, where a light was activated or increased in power in order to account for shade in ROI $350_5$. As another example, suppose the ground is particularly muddy, which may require more power by an agricultural vehicle or robot in order to move through the field. Edge computing devices such as edge computing node 234 may rely on the same power source (e.g., gasoline, battery power) as the vehicle carrying it through the field. Accordingly, it may be beneficial to deallocate computing resources from one or more tasks in order to conserve power for this movement. As an example, multiple GPUs processing high-resolution imagery using complex machine leanings models may consume considerable energy. By reducing the resolution of the imagery and/or operational parameters of the GPUs, it may be possible to conserve some power. Another example environmental condition may be temperature. On a hot day, usage of computational resources that generate heat, such as processor cycles, may be reduced in order to avoid overheating. Other computational resources that decrease heat, such as fan(s), may be operated at increased power.

At block 608, the system, e.g., by way of policy module 121, may process the state based on a policy model to generate a probability distribution over a plurality of candidate reallocation actions. These candidate reallocation action can come in numerous forms. One example might be reallocation of some quantity of RAM space from a source task to a target task. Another example may be to assign higher priorities to one or more tasks so that they are automatically allocated more processor cycles than other tasks with lower priorities. Yet another example would be to allocate additional wireless network bandwidth (e.g., via antenna $244_{1-P}$) to a remote server to a particular task, e.g., at the expense of other less-relevant or less-crucial tasks. Yet another example would be to adjust various parameters of a sensor, such as frequency, framerate, resolution, input power (which may impact accuracy), sample rate, etc. Numerous other examples are contemplated.

Based on the probability distribution, at block 610, the system, e.g., by way of policy module 121, may select and perform (or cause to be performed) one or more of the candidate reallocation actions to reallocate at least some computing resources between a first phenotypic task of the one or more phenotypic tasks and a different task while the resource-constrained device is transported through the agricultural area. In some instances, the different task may be a second phenotypic task of a plurality of phenotypic tasks. In other instances, the different task may be a new phenotypic task, outside of the one or more existing phenotypic tasks, that is initiated. In yet other instances, the different task may be a non-phenotypic task. For example, if a rover travels to an area of a field that is not yet mapped, additional resources may be reallocated to a simultaneous localization and mapping (SLAM) task, e.g., from other tasks such as phenotypic tasks.

Figure 7:
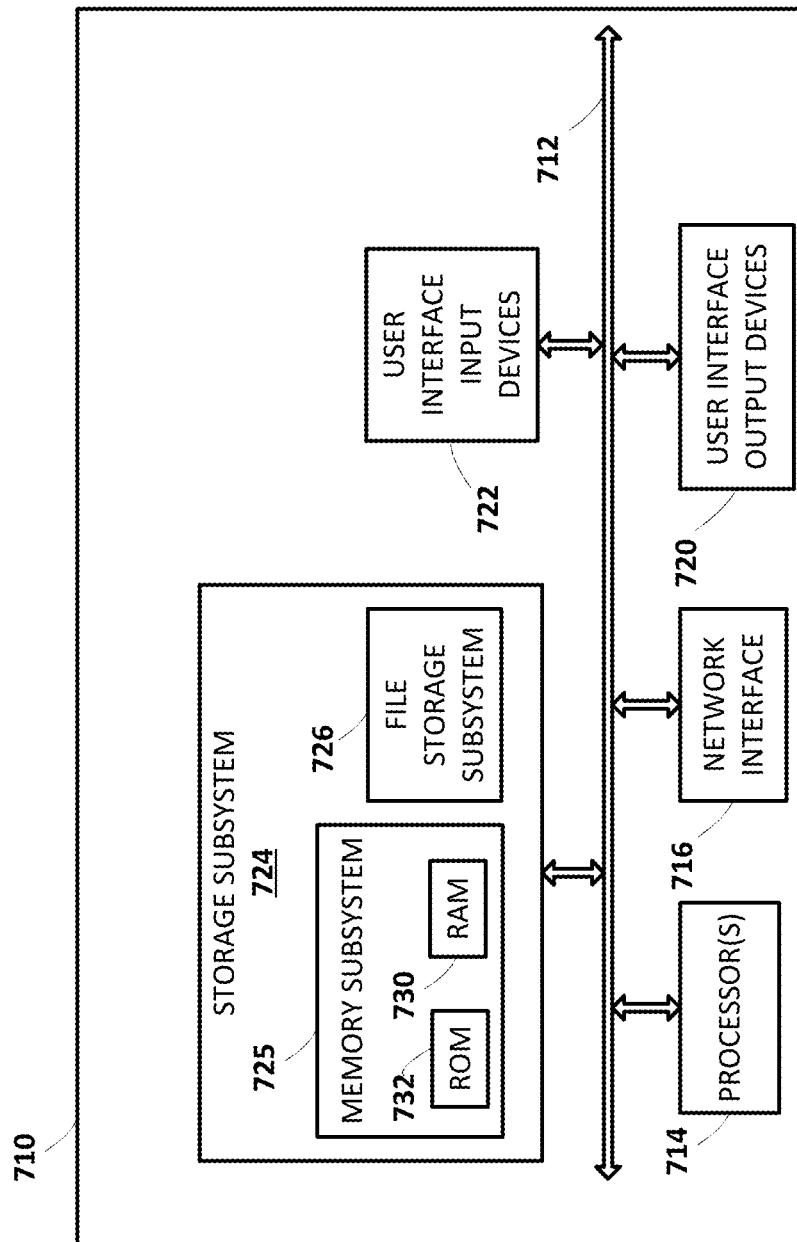
FIG. 7 schematically depicts an example architecture of a computer system.

FIG. 7 is a block diagram of an example computing device 710 that may optionally be utilized to perform one or more aspects of techniques described herein. Computing device 710 typically includes at least one processor 714 which communicates with a number of peripheral devices via bus subsystem 712. These peripheral devices may include a storage subsystem 724, including, for example, a memory subsystem 725 and a file storage subsystem 726, user interface output devices 720, user interface input devices 722, and a network interface subsystem 716. The input and output devices allow user interaction with computing device 710. Network interface subsystem 716 provides an interface to outside networks and is coupled to corresponding interface devices in other computing devices.

User interface input devices 722 may include a keyboard, pointing devices such as a mouse, trackball, touchpad, or graphics tablet, a scanner, a touchscreen incorporated into the display, audio input devices such as voice recognition systems, microphones, and/or other types of input devices. In some implementations in which computing device 710 takes the form of a HMD or smart glasses, a pose of a user's eyes may be tracked for use, e.g., alone or in combination with other stimuli (e.g., blinking, pressing a button, etc.), as user input. In general, use of the term "input device" is intended to include all possible types of devices and ways to input information into computing device 710 or onto a communication network.

User interface output devices 720 may include a display subsystem, a printer, a fax machine, or non-visual displays such as audio output devices or haptic feedback devices. The display subsystem may include a cathode ray tube (CRT), a flat-panel device such as a liquid crystal display (LCD), a projection device, one or more displays forming part of a HMD, or some other mechanism for creating a visible image. The display subsystem may also provide non-visual display such as via audio output devices. In general, use of the term "output device" is intended to include all possible types of devices and ways to output information from computing device 710 to the user or to another machine or computing device.

Storage subsystem 724 stores programming and data constructs that provide the functionality of some or all of the modules described herein. For example, the storage subsystem 724 may include the logic to perform selected aspects of the method 600 described herein, as well as to implement various components depicted in FIGS. 1, 2, 4, and 5.

These software modules are generally executed by processor 714 alone or in combination with other processors. Memory 725 used in the storage subsystem 724 can include a number of memories including a main random access memory (RAM) 730 for storage of instructions and data during program execution and a read only memory (ROM) 732 in which fixed instructions are stored. A file storage subsystem 726 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 726 in the storage subsystem 724, or in other machines accessible by the processor(s) 714.

Bus subsystem 712 provides a mechanism for letting the various components and subsystems of computing device 710 communicate with each other as intended. Although bus subsystem 712 is shown schematically as a single bus, alternative implementations of the bus subsystem may use multiple busses.

Computing device 710 can be of varying types including a workstation, server, computing cluster, blade server, server farm, or any other data processing system or computing device. Due to the ever-changing nature of computers and networks, the description of computing device 710 depicted in FIG. 7 is intended only as a specific example for purposes of illustrating some implementations. Many other configurations of computing device 710 are possible having more or fewer components than the computing device depicted in FIG. 7.

While several implementations have been described and illustrated herein, a variety of other means and/or structures for performing the function and/or obtaining the results and/or one or more of the advantages described herein may be utilized, and each of such variations and/or modifications is deemed to be within the scope of the implementations described herein. More generally, all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific implementations described herein. It is, therefore, to be understood that the foregoing implementations are presented by way of example only and that, within the scope of the appended claims and equivalents thereto, implementations may be practiced otherwise than as specifically described and claimed. Implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

What is claimed is:

1. A method implemented by a resource-constrained device while the resource-constrained device is transported through an agricultural area, the method comprising:
monitoring computing resource usage of the resource-constrained device;
monitoring phenotypic output generated by one or more phenotypic tasks performed onboard the resource-constrained device;
generating a state based on the monitored computing resource usage and the monitored phenotypic output;
processing the state based on a policy model to generate a probability distribution over a plurality of candidate reallocation actions; and
based on the probability distribution, selecting and performing one or more of the candidate reallocation actions to reallocate at least some computing resources between a first phenotypic task of the one or more phenotypic tasks and a different task while the resource-constrained device is transported through the agricultural area.

2. The method of claim 1, wherein the one or more phenotypic tasks comprise a plurality of phenotypic tasks, and the different task comprises a second phenotypic task of the plurality of phenotypic tasks.

3. The method of claim 1, wherein the different task comprises a new phenotypic task outside of the one or more phenotypic tasks.

4. The method of claim 1, wherein the state is further generated based on an amount of battery power required for the resource-constrained device to achieve one or more goals.

5. The method of claim 4, wherein the one or more goals include performance of the one or more phenotypic tasks over at least a threshold amount of the agricultural area.

6. The method of claim 1, wherein the state is further generated based on one or more environmental conditions of the agricultural area.

7. The method of claim 1, wherein the monitored phenotypic output signals potential presence of a phenotypic condition, and the different task includes application of a machine learning model trained to detect presence of the phenotypic condition.

8. The method of claim 7, wherein the phenotypic condition comprises plant disease infection or pest infestation.

9. The method of claim 7, wherein the phenotypic condition comprises plant dehydration or over-hydration.

10. The method of claim 1, further comprising causing an output device to render output conveying an effect the selected one or more candidate reallocation actions will have on the first phenotypic task.

11. The method of claim 10, wherein the output further comprises a prompt seeking approval to perform the selected one or more candidate reallocation actions.

12. The method of claim 1, wherein the selected one or more candidate reallocation actions include decreasing processor cycles assigned to the first phenotypic task and increasing processor cycles assigned to the different task.

13. The method of claim 1, wherein the selected one or more candidate reallocation actions include decreasing memory allocated to the first phenotypic task and increasing memory allocated to the different task.

14. The method of claim 1, wherein the selected one or more candidate reallocation actions include decreasing network bandwidth allocated to the first phenotypic task and increasing network bandwidth allocated to the different task.

15. The method of claim 1, wherein the selected one or more candidate reallocation actions include decreasing inter-core bandwidth allocated to the first phenotypic task and increasing inter-core bandwidth allocated to the different task.

16. A resource-constrained device configured for transportation through an agricultural area, the resource-constrained device comprising one or more processors and memory storing instructions that, in response to execution by the one or more processors, cause the one or more processors to:
monitor computing resource usage of the resource-constrained device;
monitor phenotypic output generated by one or more phenotypic tasks performed onboard the resource-constrained device;
generate a state based on the monitored computing resource usage and the monitored phenotypic output;
process the state based on a policy model to generate a probability distribution over a plurality of candidate reallocation actions; and
based on the probability distribution, select and perform one or more of the candidate reallocation actions to reallocate at least some computing resources between a first phenotypic task of the one or more phenotypic tasks and a different task while the resource-constrained device is transported through the agricultural area.

17. The resource-constrained device of claim 16, wherein the one or more phenotypic tasks comprise a plurality of phenotypic tasks, and the different task comprises a second phenotypic task of the plurality of phenotypic tasks.

18. The resource-constrained device of claim 16, wherein the different task comprises a new phenotypic task outside of the one or more phenotypic tasks.

19. The resource-constrained device of claim 16, wherein the state is further generated based on an amount of battery power required for the resource-constrained device to achieve one or more goals.

20. A non-transitory computer-readable medium comprising instructions that, in response to execution of the instructions by one or more processors of a resource-constrained device while the resource-constrained device is transported through an agricultural area, cause the one or more processors to:
monitor computing resource usage of the resource-constrained device;
monitor phenotypic output generated by one or more phenotypic tasks performed onboard the resource-constrained device;
generate a state based on the monitored computing resource usage and the monitored phenotypic output;
process the state based on a policy model to generate a probability distribution over a plurality of candidate reallocation actions; and
based on the probability distribution, select and perform one or more of the candidate reallocation actions to reallocate at least some computing resources between a first phenotypic task of the one or more phenotypic tasks and a different task while the resource-constrained device is transported through the agricultural area.

* * * * *